United States Patent [19]

Madhavan et al.

[11] Patent Number: 4,761,136

[45] Date of Patent: Aug. 2, 1988

[54] VISIBLE LIGHT CURED IMPRESSION MATERIAL

[75] Inventors: Narayanan Madhavan, Farmington Hills; Carole L. Groh, Dearborn Heights; Robert L. Probst, Ann Arbor, all of Mich.

[73] Assignee: Kerr Manufacturing Company, Romulus, Mich.

[21] Appl. No.: 82,148

[22] Filed: Aug. 6, 1987

Related U.S. Application Data

[63] Continuation-in-part of Ser. No. 890,049, Jul. 28, 1986, abandoned.

[51] Int. Cl.$^4$ ............ A61C 9/00; C08F 2/50; C08F 20/36
[52] U.S. Cl. .................... 433/214; 522/28; 522/29; 522/65; 522/90; 522/79; 522/95; 522/83; 522/23; 523/109; 524/871
[58] Field of Search ............ 522/28, 65, 90, 908, 522/79, 95, 83; 523/109; 433/214

[56] References Cited

U.S. PATENT DOCUMENTS

| | | | |
|---|---|---|---|
| 2,532,502 | 12/1950 | Joy | 523/109 |
| 4,089,763 | 5/1978 | Dart et al. | 523/115 |
| 4,182,829 | 1/1980 | Walkowiak et al. | 528/75 |
| 4,459,193 | 7/1984 | Radcliffe et al. | 522/24 |
| 4,468,202 | 8/1984 | Cohen | 433/199 |
| 4,551,486 | 11/1985 | Tateosian | 523/212 |
| 4,553,936 | 11/1985 | Wang | 433/37 |

FOREIGN PATENT DOCUMENTS 0170219 2/1986 European Pat. Off.

Primary Examiner—John C. Bleutge
Assistant Examiner—R. Dean, Jr.
Attorney, Agent, or Firm—Marjama & Pincelli

[57] ABSTRACT

A dental impression material which comprises a prepolymer formed by reacting a polyol or combination polyester polyol with a diisocyanate, and then with a hydroxyacrylate or hydroxymethacrylate; along with a metal catalyst, plasticizer, photosensitizer, reducing agent, filler and other additives. The essential characteristics of the polymer portion that makes the system work are that it is a long-chain aliphatic polyester-polyurethane molecule, which when endcapped with hydroxy arcylate moieties, is photo-polymerizable to yield a tear-resistant, highly flexible, medium-durometer elastomer, suitable for use as a dental impression material.

14 Claims, No Drawings

VISIBLE LIGHT CURED IMPRESSION MATERIAL

This application is a continuation-in-part of application Ser. No. 890,049, filed July 28, 1986, now abandoned.

BACKGROUND OF THE INVENTION

Dental elastomers used as impression materials may be generally classified as polysulfide, condensation silicone, polyvinylsiloxane or polyether types. These are normally used as a two paste system—a catalyst paste and base paste. The pastes are mixed according to the manufacturer's recommended proportions. The mixing time is generally about 30–45 seconds. The physical properties of these materials, such as flexibility, permanent deformation, compressive set, tear strength, and even shrinkage, depend upon the accuracy of the mixing ratio and how well the pastes are mixed within the specified time period. The process of mixing initiates a chemical reaction, which will result in an elastic rubber, whose physical properties and dimensional change depend upon the nature of the polymerization reaction. The mixing also results in the incorporation of entrapped air. These air bubbles, together with those already in the material due to the manufacturing process, reduce the accuracy and readability of the impression.

It is therefore an object of the present invention to provide a bubble free single component paste for dental impression taking. It is also the object of this invention to provide a low shrinkage impression paste for obtaining accurate impressions. It is also another object of this invention to provide an impression material which can be cured by exposure to visible light of the appropriate wavelength in the range of about 400–600 nanometers.

SUMMARY OF THE INVENTION

The present invention is directed to a one-component elastomeric dental impression material which can be cured by exposure to radiation of suitable wavelengths. This material is based on urethane acrylates.

More specifically, the impression material comprises a pre-polymer formed by reacting a polyol or combination polyester/polyol, a diisocyanate, and a hydroxyacrylate or hydroxymethacrylate; along with a metal catalyst, plasticizer, photosensitizer, reducing agent, filler and other additives. The essential characteristics of the polymer portion that makes the system work are that it is a long-chain aliphatic polyester-polyurethane molecule, which when endcapped with hydroxy acrylate moieties, is photo-polymerizable to yield a tear-resistant, highly-flexible, medium-durometer elastomer, suitable for use as a dental impression material. The impression materials, according to this invention, meet all the requirements of the American Dental Association specification number 19 for Type I materials. The fully cured material has very low dimensional change, good compression set, and strain in compression. The stone models have smooth, bubble-free surfaces.

DETAILED DESCRIPTION OF THE INVENTION

The impression material of the present invention is composed of the following: A difunctional polyol or combination polyester/polyol, having a preferred molecular weight of about 1500 to 3000. All suitable polyols which are essentially aliphatic in nature and of appropriate molecular weight to provide the desired low level of crosslinking in the resultant polymer may be used. Polyester/polyetherdiols are preferred since the corresponding triols and tetrols would significantly increase the crosslink density of the resulting polymer and produce elastomers too rigid for use as dental impression materials.

A diisocyanate, aliphatic or aromatic in nature, such as 2,4 toluenediisocyanate, 2,6 toluenediisocyanate, or mixtures thereof, hexamethylene-diisocyanate, isophorone diisocyanate, trimethylhexamethylenediisocyanate, methylenediisocyanate, and cyclohexylmethanediisocyanate are examples of suitable diisocyanates. Isocyanatoethylmethacrylate may also be used in a single step reaction. Hexamethylene diisocyanate is preferred because of its straight chain aliphatic nature.

Another reactant according to the present invention is a low molecular weight hydroxyacrylate or hydroxymethacrylate that terminates the polyurethane at each end. Typical materials include hydroxyethylacrylate, hydroxyethylmethacrylate and hydroxypropyl-methacrylate.

The polyol to diisocyanate to hydroxy acrylate ratio is theoretically about 1:2:2, however to compensate for the various purity levels of the ingredients and to ensure that the final prepolymer contains no free isocyanate groups, when assayed by titration, a slight modification of this theoretical ratio is used.

The reaction between NCO and OH is generally promoted by a metal catalyst or amine catalyst. Even though a tertiary amine is present in the system, as mentioned later, a small amount of metal catalyst, especially tin in the form of dibutyltindilaurate or stannous octoate, is employed. The urethane reaction between NCO and OH is highly exothermic and the uncatalyzed reaction is extremely slow. In the presence of a plasticizer, which typically is about 35 percent of the formulation, the temperature rise is well controlled to prevent possible side reactions, including the polymerization of the acrylic compound.

Even though other plasticizers may be employed successfully, Santicizer 261 (Octyl Benzyl Phthalate) available from Monsanto Chemical Company is particularly suitable. This is an alkylbenzyl-phthalate, the alkyl group having 7 to 9 carbon atoms.

Another material used is a high molecular weight anti-oxidant having hindered phenolic groups. This material has no apparent reaction with isocyanates.

A small amount of surfactant such as Modaflow is also employed. This clear viscous liquid is a copolymer of ethylacrylate and 2-ethylhexylacrylate.

The classification of the limited family of surface active agents or modifiers of which "Modaflow" is a chosen example would be "acrylate or methacrylate polyesters or copolymers thereof".

The following compositions represent typical materials which are suitable for use as surfactants with the present invention.

| Composition | CAS Number |
| --- | --- |
| Ethyl Acrylate - Butyl Acrylate Copolymer | 26355-42-4 |
| Ethyl Acrylate - 2 ethylhexyl Acrylate Copolymer | 26376-86-3 |
| Ethyl Acrylate - Ethyl Methacrylate - Methyl Acrylate Copolymer | 67953-70-2 |
| Ethyl Acrylate - Homopolymer | 9003-32-1 |
| Ethyl Acrylate - 2-Hydroxyethyl Methacrylate - Methyl Methacrylate Copolymer | 27012-37-9 |
| Ethyl Acrylate - Methyl Acrylate Copolymer | 9010-87-1 |
| Ethyl Acrylate - Methyl Acrylate - Methyl Methacrylate Copolymer | 30395-18-7 |
| Ethyl Acrylate - Methyl Methacrylate - Butyl Acrylate Copolymer | 25167-43-5 |
| Ethyl Acrylate - Methyl Methacrylate Copolymer | 9010-88-2 |
| Methyl Methacrylate - Butyl Acrylate Copolymer | 25852-37-3 |
| Methyl Methacrylate - Butyl Acrylate - Ethyl Acrylate - 2-Hydroxyethylacrylate Copolymer | 33395-08-3 |
| Methyl Methacrylate - Butyl Acrylate - Hydroxyethylmethacrylate Copolymer | 25951-39-7 |
| Methyl Methacrylate - Butyl Acrylate - 2 Hydroxypropylacrylate Copolymer | 67874-30-0 |
| Methyl Methacrylate - Butyl Methacrylate Copolymer | 25608-33-7 |
| Methyl Methacrylate - Butyl Methacrylate - Hydroxy Propylmethacrylate Copolymer | 67874-31-1 |
| Methyl Methacrylate - Ethyl Acrylate - Butyl Acrylate Copolymer | 25767-43-5 |
| Methyl Methacrylate - Ethyl Acrylate - Butyl Methacrylate Copolymer | 40471-03-2 |
| Methyl Methacrylate - 2 ethylhexyl Acrylate, Butyl Methacrylate, Butyl Acrylate Copolymer | 68334-73-6 |

The isocyanate content of the pre-polymer formed by reacting the polyol, diisocyanate and hydroxyacrylate or methacrylate, should be zero. In order to achieve this condition, the amounts of reactants should be balanced stoichiometrically. That is, the sum of hydroxy equivalents of polyol and hydroxyacrylate or methacrylate should be equal to the isocyanate equivalent. A good elastomeric rubber is obtained if the hydroxy equivalent of the acrylyl, chain terminator, is either equal to or lower than that of the polyol.

A photosensitizer is added to the reaction mix in order to cure it by actinic radiation in the range between about 400-600 nanometers. Typical photosensitizers include benzophenone, acetophenone, thioxanthen-9-one, 9-fluorenone, anthraquinone, 4′methoxyacetophenone, diethoxyacetophenone and the diketones, such as biacetyl, 2,3 pentanedione, benzil, 4,4′methoxybenzil, 4,4′oxidibenzil, and dl camphorquinone. Camphorquinone and diketones absorb mostly in the visible light spectrum between 400 and 500 nanometers. Formulations with these initiators cure readily with visible radiation.

The dental impression materials also contain a reducing agent which reduces the ketonic photosensitizers when they are in the excited state and accelerates the rate of polymerization. These reducing agents also reduce the surface tackiness of the cured elastomer. These materials comprise organic amines, aliphatic or aromatic, monoamines, or polyamines, primary, secondary or tertiary. The tertiary amines are generally preferred. Suitable tertiary amines are described U.S. Pat. No. 3,759,807 which is incorporated herein by reference. Tertiary amines with additional functional groups are also employed such as 4,4′bis(dimethylamino)benzophenone, N-methyldi-ethanolamine, 4 dimethylaminobenzoate, dimethylaminobenzaldehyde, di-methylaminoethylmethacrylate and dimethylaminoethylacrylate.

Another important component of the dental impression material is the filler which provides added strength and increases the accuracy of the impression. Suitable fillers include talc, calcium carbonate, zinc oxide, glass powder, quartz, and mixtures thereof. Silica, especially synthetic silica, because of its higher purity, which has a refractive index very close to 1.46, is a preferred material in that its refractive index matches very closely to that of the liquid matrix to maximize light energy transmission in order to maximize the curing efficiency of the material. Aerosil R-972, a hydrophobic submicron synthetic amorphous precipitated silica from DeGussa, may be used alone or in combination with other coarser types of silica. Quso WR 55 from PQ Corporation, a synthetic amorphous precipitated silica of average particle size of about 3 to 4 microns, may also be employed. A combination of Aerosil R-972 and Quso is preferred. In general, the concentration of the filler is about 5 to 20% by weight of the impression material.

In order to further reduce the tackiness due to air inhibition, a small amount of low temperature melting wax which seems to act synergistically with the tertiary amine can be added to the mix. This addition results in a dry, smooth and easy-to-read surface. Readability can be further enhanced by coloring the material with a dye or pigment.

The following example illustrates one embodiment of the present invention. The percentages and parts are by weight.

EXAMPLE 1

| | | Broad Concentration Range By Wt. % | Specific Formulation |
| --- | --- | --- | --- |
| Polymer | Rucoflex polyesterdiol S-1011-55* | 20-50 | 60.000 parts (.06 equiv.) |
| | Toluene diisocyanate (Aldrich) | 5-20 | 8.700 parts (.1 equiv.) |
| | 2-hydroxypropylmethacrylate | 5-20 | 5.760 parts (.04 equiv.) |
| Plasticizer | Santicizer 261 (Monsanto) | 20-50 | 44.500 parts |
| Fillers | Quso 55 (PQ Corporation) | 5-20 | 9.000 parts |
| | Aerosil R972 (DeGussa) | 5-20 | 2.500 parts |
| Additives | Dibutyltindilaurate (M & T) | .01-0.5 | .050 parts |

| | | Broad Concentration Range By Wt. % | Specific Formulation |
|---|---|---|---|
| | Irganox 1010 (Ciba Giegy)** | .01–0.5 | .025 parts |
| | Modaflow (Monsanto)*** | .05–0.2 | .120 parts |
| | (Plus Paraffin Wax and Pigment) | | |
| Curing | dl Camphroquinone (Aldrich) | .01–1.0 | .080 parts |
| System | Dimethylaminobenzaldehyde | .01–1.0 | .060 parts |

*A polymeric 2, 2'-oxybis [ethanol] hexanedioic acid ester. ($C_6H_{10}O_4C_4H_{10}O_3$)
**Tetrakis (Methylene (3, 5-Di-Tert-Butyl-4-Hydroxy hydrocinnamate)) Methane
*** Ethyl acrylate and 2-ethyl hexyl acrylate copolymer The specific formulation listed above is prepared by the following procedure:

The Santicizer 261 and polyesterdiol are evacuated for three hours at 85° C. to free the materials from moisture to minimize unwanted side reactions. The fillers are heated in an oven at 150° C. for two hours prior to use. All other chemicals are employed in the as received condition except the paraffin wax, which, when optionally used is melted and deaerated for three hours at 85° C. During evacuation, the vacuum is maintained at at least 1 mm of mercury. The plasticizer is placed in a glass flask and the dimethylaminobenzaldehyde is dissolved in it. The Aerosil is then incorporated and then the Quso. The polyesterdiol is then added and mixed thoroughly. The toluenediisocyanate is then added, at which time the mixture is a mobile liquid. The minor ingredients, such as dibutyltindilurate, Irganox 1010, Modaflow and camphroquinone, are dissolved in the 2-hydroxypropylmethacrylate by heating in an oven at 50° C. for half an hour. They are added after cooling to room temperature. The mix was kept in a dark room during and after preparation.

As the R'NCO+OHR→R'NHCOOR, urethane reaction proceeds, the viscosity of the mix increases, then stabilizes when the reaction is completed. At the end of the reaction, the NCO concentration should be zero. The NCO concentration can be monitored either by titration technique as described in ASTM 1638 or by infrared spectroscopy. It takes approximately five to seven days to complete the urethane reaction. The paste is readily cured by the visible light energy emitted by a 275 watt General Electric sun lamp three inches away from the material.

The following example illustrates another embodiment of the present invention.

EXAMPLE 2

| | |
|---|---|
| Rucoflex S-1011-55 | 456.0 parts (.456 equiv.) |
| 1,6 Hexanediisocyanate | 63.8 parts (.760 equiv.) |
| 2-Hydroxypropylmethacrylate | 43.8 parts (.304 equiv.) |
| Santicizer 261 | 338.0 parts |
| Dimethylaminobenzaldehyde | 4.6 parts |
| Aerosil R-972 | 19.0 parts |
| Quso | 68.4 parts |
| Dibutyltindilurate (T-12) | 0.4 parts |
| Irganox 1010 | 0.2 parts |
| Modaflow | 0.9 parts |
| Camphroquinone | 0.6 parts |
| Meteor Cobalt Blue (Harshaw Chemical) | 2.0 parts |

A one kilogram batch was made using the above formula. The raw materials were purified as in example 1. The dimethylaminobenzaldehyde was dissolved in Santicizer 261 and the Cobalt blue pigment thoroughly dispersed. After incorporating the Aerosil and Quso, the paste was roll milled twice. The milled material was placed in a one gallon chrome plated mixing bowl of a Ross vacuum mixer with planetary blades. Corrections were made for material loss due to roller milling. The subsequent additions are made in this bowl and the photoinitiator is added in a dark room where the radiation capable of curing the material is completely eliminated. Mixing and evacuation is begun. Evacuation is continued for only five minutes once the vacuum reached 28 inches. The mix froths under high vacuum and continues to froth until the vacuum is released. The liquid is transferred into a light-proof metal container in a dark room.

After seven days the reaction between the OH and NCO is completed, as denoted by zero NCO content. Paste is placed in a "4-In-One Tray" (Kerr/Sybron) made of polystyrene, and an impression made using a typodont. The light source used is the same as described in Example 1, and the exposure time is five minutes.

The following tests were made according to the ADA specifications, with slight modifications in sample preparation. Consistency of this single paste at 20° C. is 42 mm (ADA 4.3.4.). A transparent cylindrical plexi-glass mold, 12.5 mm inside diameter and 20 mm high, was filled with the material and the ends flattened with 1 mm thick glass plates. The sample was cured by exposing the ends to the above mentioned light at three inches away from the light source. The temperature rise on the material was minimized by a fan placed alongside the sample. The results are shown below:

| | Total Cure Time: | |
|---|---|---|
| | 4 Minutes (2 min. each end) | 5 Minutes (2½ min. each end) |
| Compression Set % | 0.2 | 0.1 |
| Strain in Compression % | 3.8 | 3.8 |
| Flow | — | 0.2 |
| 24 Hour Dimensional Change % | — | 0.15 |
| Detail Reproduction 0.020 mm | — | Pass |
| Compatibility with Gypsum (Vel-Mix) 0.020 mm | — | Pass |
| Compatibility with Silver Plating Solution | — | Pass |
| 7 day 60° C. Deterioration | | Pass |

Details of test procedure are given in the Journal of the American Dental Association, Volume 94, April 1977.

The following example illustrates a further embodiment of the present invention.

EXAMPLE 3

| | |
|---|---|
| Santicizer 261 | 338.00 parts |
| FD & C Blue #1* | .25 parts |
| Dimethylaminobenzaldehyde | 4.60 parts |
| Paraffin Wax | 20.00 parts |
| Aerosil | 19.00 parts |
| Quso 55 | 68.40 parts |
| Rucoflexpolyesterdiol S-1011-55 | 456.00 parts (.456 equiv.) |

| | |
|---|---|
| 1,6-hexamethylenediisocyanate | 63.80 parts (.760 equiv.) |
| 2-hydroxypropylmethacrylate | 43.80 parts (.304 equiv.) |
| Modaflow | 0.90 parts |
| Irganox 1010 | 0.20 parts |
| Dibutyltindilaurate | 0.40 parts |
| Camphroquinone | 1.00 parts |

*Disodium salt of ethyl [4-[p-[ethyl (m-sulfobenzyl)-amino]-oc- (o-sulfophenyl) benzylidene]-2,5-cyclohexadien-1-ylidene] m-sulfobenzyl) ammonium hydroxide The preparation of the above formulation is made in the same manner as in the previous sample. The paraffin wax was melted and added to the plasticizer and stirred rapidly prior to the addition of fillers. Adjustments in the filler/plasticizer ratio are used to develop a multiviscosity system. That is, a higher ratio is used to produce a heavy bodied viscosity material, while a lower ratio is used to produce a light bodied viscosity material. Therefore, a variety of materials can be developed to suit a variety of dental applications and techniques.

While the invention has been described in detail with respect to specific embodiments thereof, it will be understood by those skilled in the art that variations and modifications may be made without departing from the essential features thereof.

What is claimed is:

1. A one component photopolymerizable elastomeric impression material comprising:

| | Weight Percent |
|---|---|
| (a) a pre-polymer formed by reacting a polyol or a combination polyester/polyol with a diisocyanate, and then a hydroxyacrylate or hydroxymethacrylate; | 20–65 |
| (b) a metal catalyst; | 0.01–1.0 |
| (c) a plasticizer; | 20–50 |
| (d) a photosensitizer; | 0.1–1.0 |
| (e) a reducing agent; | 0.1–1.0 |
| (f) a filler | 5–20 |

2. The impression material of claim 1 which further includes:

| | Weight Percent |
|---|---|
| (g) an antioxidant | 0.01–1.0 |
| (h) a surfactant which comprises an acrylate or methacrylate polyester or copolymer thereof | 0.05–2.0 |
| (i) a wax having a low melting point; and | 0.1–4.0 |
| (j) a dye or pigment | 0.01–2.0 |

3. A one-component photopolymerizable elastomeric impression material comprising:

| | Weight Percent |
|---|---|
| Polyesterdiol | 20–50 |
| Hexamethylene diisocyanate | 5–20 |
| Hydroxy propylmethacrylate | 5–20 |
| Alkylbenzylphthalate | 20–50 |
| Dimethyl aminobenzaldehyde | .01–1.0 |
| Silica | 5–20 |
| Camphoroquinone | .01–1.0 |

4. The impression material of claim 3 wherein the silica is a synthetic submicron silica.

5. The impression material of claim 3 wherein the silica is a synthetic micronized silica.

6. The impression material of claim 3 wherein the silica is a combination of synthetic submicron and micronized silica.

7. The impression material of claim 6 which contains an antioxidant in a concentration range of about 0.01–1.0 weight percent.

8. The impression material of claim 6 which contains a surfactant which comprises an acrylate or methacrylate polyester or copolymer thereof.

9. The impression material of claim 6 which contains a wax having a low melting point in a concentration range of about 0.1–4.0 weight percent.

10. The impression material of claim 6 which contains a dye or pigment in a concentration range of about 0.01–2.0 weight percent.

11. The impression material of claim 6 which further includes:
(g) an antioxidant;
(h) a surfactant which comprises an acrylate or methacrylate polyester or copolymer thereof,
(i) a wax having a low melting point; and
(j) a dye or pigment.

12. The impression material of claim 6 wherein the filler/plasticizer ratio are adjusted to vary the viscosity of the system.

13. A dental impression which is made by placing a one component photopolymerizable elastomeric impression material comprising a pre-polymer formed by reacting a polyol or a combination polyester/polyol with a diisocyanate; and then with a hydroxyacrylate or hydroxymethacrylate, a metal catalyst, a plasticizer, a photosensitizer, a reducing agent and a filler in a light transmitting dental impression tray, properly seating the tray in a patient's mouth, and exposing the tray to visible light for five minutes or less to cure said material.

14. The dental impression of claim 13 which further contains a surfactant which comprises an acrylate or methacrylate polyester or copolymer thereof.

* * * * *